US010292484B1

United States Patent
LaRosa et al.

(10) Patent No.: US 10,292,484 B1
(45) Date of Patent: May 21, 2019

(54) APPARATUS AND METHOD FOR NON-INVASIVE REPOSITIONING OF SAGGING SKIN, CELLULITE AND FAT TISSUE ON THIGHS, ARMS, STOMACH AND BUTTOCKS

(71) Applicants: Penilopee Lee LaRosa, Oldsmar, FL (US); Nicholas LaRosa, Oldsmar, FL (US)

(72) Inventors: Penilopee Lee LaRosa, Oldsmar, FL (US); Nicholas LaRosa, Oldsmar, FL (US)

( * ) Notice: Subject to any disclaimer, the term of this patent is extended or adjusted under 35 U.S.C. 154(b) by 438 days.

(21) Appl. No.: 13/786,615

(22) Filed: Mar. 6, 2013

Related U.S. Application Data

(62) Division of application No. 12/340,000, filed on Dec. 19, 2008, now abandoned.

(60) Provisional application No. 61/008,849, filed on Dec. 26, 2007, provisional application No. 61/192,124, filed on Sep. 16, 2008.

(51) Int. Cl.
*A45D 44/22* (2006.01)
*A61F 13/02* (2006.01)

(52) U.S. Cl.
CPC .................................... *A45D 44/22* (2013.01)

(58) Field of Classification Search
CPC ...................................................... A45D 44/22
See application file for complete search history.

(56) References Cited

U.S. PATENT DOCUMENTS

| 363,538 | A | * | 5/1887 | Penny ........................... 606/215 |
|---|---|---|---|---|
| 2,399,545 | A | | 4/1946 | Davis |
| 4,430,998 | A | | 2/1984 | Harvey et al. |
| 4,432,347 | A | * | 2/1984 | Clavin ................ A61F 9/00718 128/898 |
| 4,706,661 | A | | 11/1987 | Barrett |
| 4,926,850 | A | | 5/1990 | Lott et al. |
| 5,012,801 | A | | 5/1991 | Feret |
| 5,116,675 | A | * | 5/1992 | Nash-Morgan ................. 602/74 |
| 5,985,395 | A | | 11/1999 | Comstock et al. |
| 6,159,497 | A | | 12/2000 | LaPrade et al. |
| 6,190,346 | B1 | * | 2/2001 | McGill .................. A45D 44/22 602/54 |
| 6,666,747 | B1 | * | 12/2003 | Buntz .................... A41C 3/065 424/400 |
| 7,399,216 | B2 | | 7/2008 | Mateo |
| 7,473,158 | B2 | | 1/2009 | Horton |
| 7,608,090 | B2 | * | 10/2009 | Matsui .................. A45D 44/22 602/1 |
| 7,951,443 | B2 | * | 5/2011 | Esaki .............................. 602/47 |
| 8,183,428 | B2 | | 5/2012 | Gurtner et al. |
| 8,624,076 | B2 | * | 1/2014 | Beaudry ........................ 602/41 |
| 2004/0138699 | A1 | | 7/2004 | Lish |
| 2006/0046592 | A1 | | 3/2006 | Novelli |

(Continued)

*Primary Examiner* — Julian W Woo
(74) *Attorney, Agent, or Firm* — Thomas | Horstemeyer, LLP

(57) ABSTRACT

An apparatus and a method for non-invasive repositioning of sagging skin, cellulite and fat tissue. The apparatus includes a flexible tape having at least three sections. The first segment includes an adhesive and a removable liner thereon. An opposed second segment includes an adhesive and a removable liner thereon. An intermediate segment is located between the first and second segments which is devoid of adhesive.

7 Claims, 3 Drawing Sheets

(56) References Cited

U.S. PATENT DOCUMENTS

2008/0228217 A1\* 9/2008 Friend .................... A45D 44/22
606/204.35

\* cited by examiner

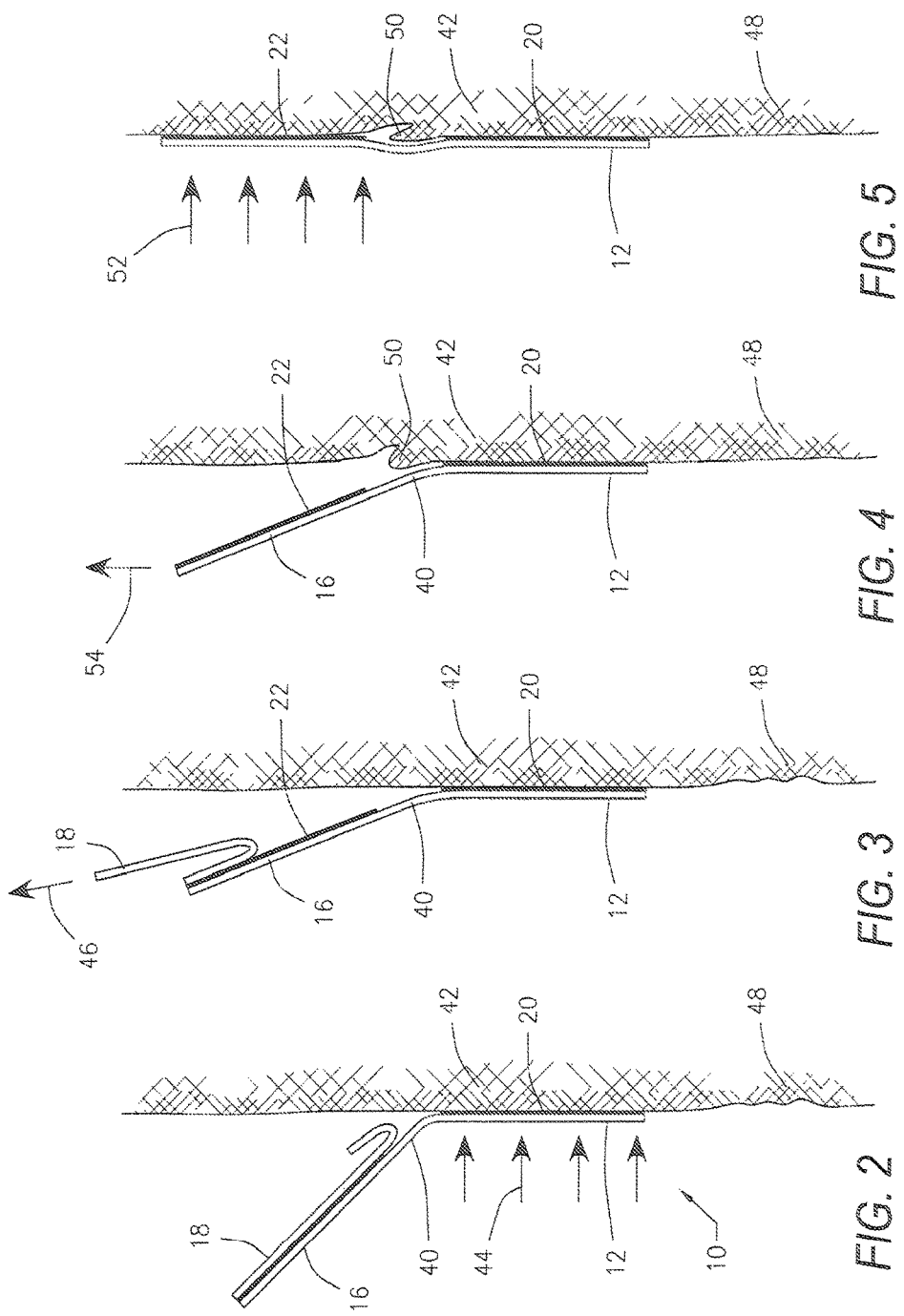

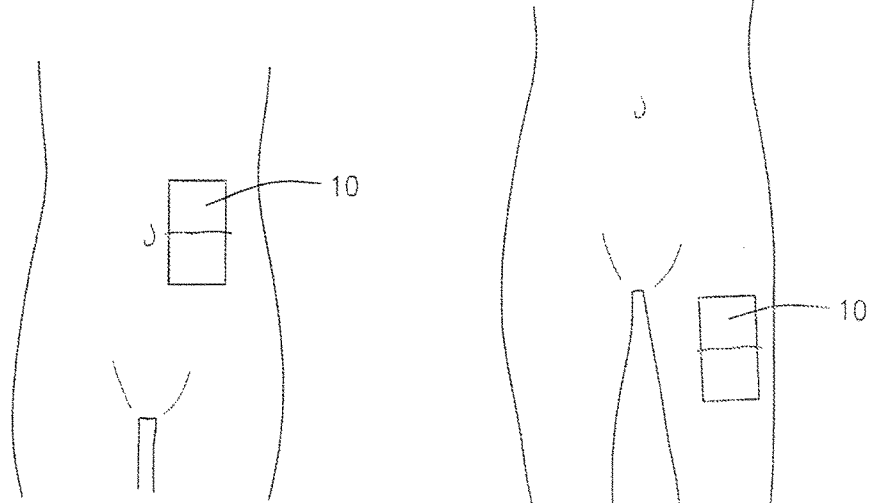
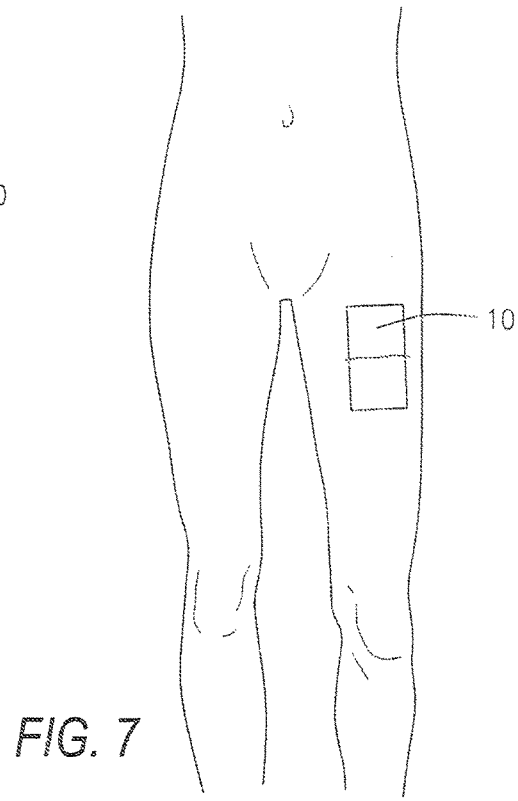
FIG. 6
FIG. 7
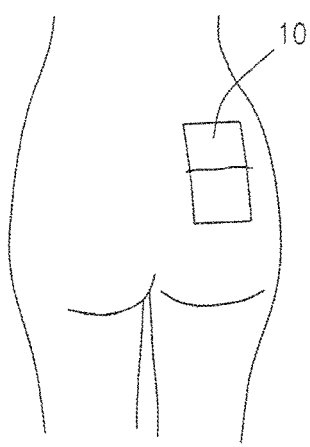
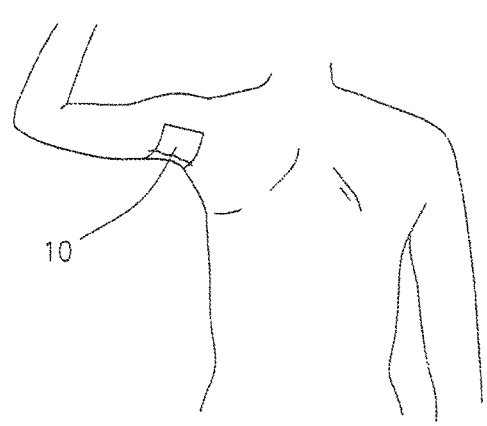
FIG. 8
FIG. 9

APPARATUS AND METHOD FOR NON-INVASIVE REPOSITIONING OF SAGGING SKIN, CELLULITE AND FAT TISSUE ON THIGHS, ARMS, STOMACH AND BUTTOCKS

CROSS-REFERENCE TO PENDING APPLICATION

This application is a divisional application of U.S. patent application Ser. No. 12/340,000 filed Dec. 19, 2008, which claims priority to U.S. Provisional Patent Application Ser. No. 61/008,849 filed Dec. 26, 2007, and Provisional Patent Application Ser. No. 61/192,124 filed Sep. 16, 2008, incorporated herein by reference.

BACKGROUND OF THE INVENTION

1. Field of the Invention

The present invention relates to both an apparatus and a method for repositioning of sagging skin, cellulite and fat tissue on thighs, arms, stomach and buttocks.

2. Prior Art

There are widespread cosmetic concerns about sagging skin, cellulite and fat tissue. The marketplace is full of treatments that advertise solutions to these issues.

The causes of sagging skin include heredity and aging. For example, it is known that skin becomes thinner with aging and does not appear as tight.

With cellulite, the skin appears dimpled. The causes for occurrence of cellulite are poorly understood but are believed to include gender, race, predisposition to circulatory issues, diet, lifestyle, and other factors.

Various types of solutions and therapies have been suggested to these issues although there is little scientific evidence to support most of the claims.

Orally delivered vitamins and pharmacological agents have been suggested. Additionally, various dermal creams have been suggested. Injections of pharmaceuticals and vitamins into the skin have also been suggested.

Physical massage and manipulation and other mechanical methods have been tried. Laser and radio frequency treatments of various sorts have also been tried. Finally, various surgical procedures including liposuction are known.

Many of these therapies lack scientific proof of success and some may be dangerous.

Other non-invasive proposals for skin application include 'Thigh Sliders Shields for Upper-Inner Thighs", U.S. Patent Application Publication No. 2006/0046592 directed to the problem of chafing on the inner thighs, and "Method, Adhesive Sheet, and Kit Configured to Lift and Shape a Female Human Breast", U.S. Pat. No. 7,399,216.

It would be advantageous to provide an apparatus and method for non-invasive temporary repositioning of skin.

Accordingly, the present invention is directed to temporarily repositioning the skin to reduce the visual affects of sagging skin, cellulite or fat tissue.

The present invention is directed to a non-invasive apparatus and a method of application which is extremely simple to apply and cost-effective.

The present invention is also directed to a non-invasive apparatus that may be worn under clothing without skin irritation or injury.

SUMMARY OF THE INVENTION

The present invention is directed to an apparatus and a method for non-invasive repositioning of sagging skin, cellulite and fat tissue. The apparatus includes a first segment fabricated from a thin, flexible film or tape with an adhesive applied on one side. A removable liner covers the adhesive on the first segment prior to installation. A second segment is opposed to the first segment and is likewise composed of a thin, flexible film or tape. The second segment likewise includes an adhesive on one side and a removable liner thereon which covers the adhesive.

In a preferred embodiment, juxtaposed between the first segment and the second segment is an intermediate segment. In a preferred embodiment, the intermediate segment is devoid of any adhesive.

In order to apply and install, the removable liner of the first segment is removed exposing the adhesive thereon. The first segment is then applied to the skin in a desired location so that the first segment is adhesively connected to the skin by adhesive. Thereafter, the removable liner is removed from the second segment so that the adhesive thereon is revealed.

The second segment will be held and gently lifted upward. This action will cause the skin attached to the first segment to also move upward and cause the skin below the first segment to be lifted, tightened, repositioned and smoothed. This upward action will also cause a small portion of the skin above the first segment to lap or fold over itself. The skin fold will coincide with the intermediate segment.

Thereafter, the second segment with the adhesive exposed will be applied and secured to the skin by pressing the second segment against the skin. Accordingly, the folded over skin is retained therein.

BRIEF DESCRIPTION OF THE DRAWINGS

FIGS. 2, 3, 4 and 5 illustrate the sequential method of application of the apparatus shown in FIG. 1 for non-invasive repositioning of sagging skin, cellulite and fat tissue;

FIG. 6 illustrates the apparatus shown in FIG. 1 applied to the skin of an individual on the stomach;

FIG. 7 illustrates the apparatus shown in FIG. 1 applied to the skin of an individual on an upper thigh;

FIG. 8 illustrates the apparatus shown in FIG. 1 applied to the skin of an individual on the buttocks; and FIG. 9 illustrates the apparatus shown in FIG. 1 applied to the skin of an individual on the arm.

DETAILED DESCRIPTION OF THE PREFERRED EMBODIMENTS

Figure 1:
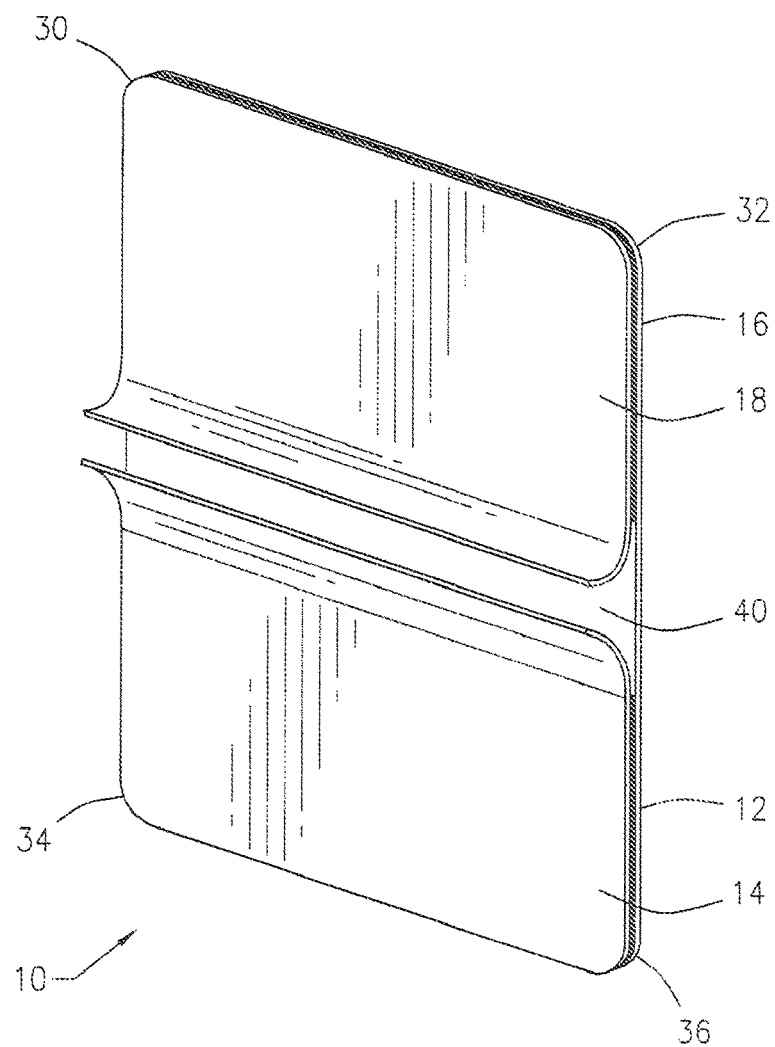
FIG. 1 is a perspective view of an apparatus for non-invasive repositioning of sagging skin, cellulite and fat tissue constructed in accordance with the present invention.

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Referring to the drawings in detail, FIG. 1 illustrates a perspective view of an apparatus 10 for non-invasive repositioning of sagging skin, cellulite and fat tissue. The apparatus 10 is shown prior to application on an individual. The apparatus 10 includes a first segment 12 fabricated from a thin, flexible film or tape with an adhesive applied on one side (the adhesive not visible in FIG. 1). The flexible film or tape is conformable to the body of the individual. A removable liner 14 covers the adhesive on the first segment 12.

A second segment 16 of the apparatus 10 is opposed to the first segment and is likewise composed of a thin, flexible film or tape. The second segment 16 likewise includes an adhesive on one side of the second segment (the adhesive not visible in FIG. 1) and a removable liner 18 thereon which covers the adhesive.

The removable liners 14 and 18 may be fabricated from paper, plastic or other thin material and may be of the crack and peel off variety.

The flexible film or tape of the first and second segment may be fabricated from polyethylene, polycarbonate, other polymers, or other flexible, lightweight material.

The adhesive may be a hypo-allergenic, pressure sensitive adhesive. In one preferred embodiment, a silicone polymer gel adhesive is employed. In another embodiment, the adhesive is an acrylate.

The first and second segments may each have rounded external corners as shown at 30, 32, 34 and 36. The rounded corners discourage dislodgment of the apparatus 10 from the skin after application (to be described herein). The apparatus may be square shaped or rectangular shaped.

In a preferred embodiment, juxtaposed between the first segment 12 and the second segment 16 is an intermediate segment 40. The intermediate segment 40 may be fabricated from the same tape or film material as the first segment and the second segment. In a preferred embodiment, the intermediate segment 40 is devoid of any adhesive. In general, the intermediate segment 40 will be smaller than either the first or second segment.

The flexible tape of the first segment 12 and the second segment 16, as well as the intermediate segment 10, may be translucent or even transparent. Likewise, the adhesive on the first segment and the second segment may be translucent or even transparent.

The apparatus 10 may be stored and shipped in the configuration shown in FIG. 1.

FIGS. 2 through 5 illustrate the sequential method of application of the apparatus 10 shown in FIG. 1. Initially, the skin 42 where the apparatus 10 is to be applied should be freshly washed, dry and free from any and all lotions, powders, deodorants, or oils.

The removable liner 14 of the first segment 12 is removed exposing the adhesive. As shown in FIG. 2, the first segment 12 is then applied to the skin 42 so that the first segment 12 is adhesively connected to the skin 42 by adhesive 20, as illustrated by arrows 44. The back of the first segment may be rubbed so that good adhesion with the skin is achieved.

It is possible to save the removable liner 14 for reuse. At this stage, the second segment 16 is not attached to the skin and the removable liner 18 therefor is still in place.

Thereafter, as shown in FIG. 3, the removable liner 18 is removed from the second segment 16 as illustrated by arrow 46 so that adhesive 22 is revealed.

Continuing on to FIG. 4, the second segment 16 will be held with the adhesive 22 thereon exposed and gently lifted upward as illustrated by arrow 48. This action will cause the skin 42 attached to the first segment 12 to also move upward. This action will cause the skin 48 below the first segment 12 to be lifted, tightened, repositioned and smoothed.

This upward action will also cause a small portion of skin between the first segment 12 and the second segment 16 to lap or fold over itself as shown at 50. The skin fold will coincide with the intermediate segment 40. Thereafter, the second segment 16 with the adhesive exposed will be applied and secured to the skin by pressing the second segment 16 against the skin as shown by arrow 54. Accordingly, the folded over skin is retained without any binding or pinching caused by adhesive on the folded skin. The excess skin folds beneath the intermediate segment 10 which is devoid of adhesive.

The apparatus 10 may be applied and worn under garments, such as shorts, shirts or blouses.

FIGS. 6 through 9 illustrate non-limiting examples of the usage of the apparatus 10 of the present invention.

FIG. 6 illustrates application of the apparatus 10 of the invention to the stomach area of an individual. The apparatus 10 may be worn beneath clothing or sportswear.

FIG. 7 illustrates the application of the apparatus 10 to an upper thigh of an individual. The apparatus may be worn under shorts or a skirt so that the skin below appears smooth and taut.

FIG. 8 illustrates the application of the apparatus 10 to buttocks of an individual.

Finally, FIG. 9 illustrates the application of the apparatus 10 of the present invention to an arm of an individual to lift the skin around the triceps.

Following application and usage, the apparatus 10 may be removed by unfastening one or more corners and then peeling the apparatus 10 away from the skin. The apparatus may be formulated with adhesive that may be reused. Therefore, the apparatus 10 may be washed and reused a number of times. After washing, the apparatus 10 will be dried and the removable liners may be reapplied.

The present invention has been found to be a simple, cost-effective and non-invasive method to reposition skin in order to lift, tighten, and smooth.

Whereas, the present invention has been described in relation to the drawings attached hereto, it should be understood that other and further modifications, apart from those shown or suggested herein, may be made within the spirit and scope of this invention.

What is claimed is:

1. A method for non-invasive repositioning of sagging skin, cellulite and fat tissue, which method comprises:
    removing a releasable liner from a first segment of continuous flexible tape comprising a single uniform material to reveal an adhesive on said first segment;
    attaching said first segment of said continuous flexible tape to skin of an individual;
    pulling an opposed second segment of said continuous flexible tape to reposition said skin;
    removing a releasable liner from said second segment of said flexible tape wherein said second segment includes an adhesive; and
    causing a portion of skin between said first segment and said second segment to be lapped over another portion of skin; and
    attaching said second segment of said tape to said skin, where the portion of skin that is lapped over the other portion of skin is covered by an intermediate segment of said continuous flexible tape, where the intermediate segment is intermediate of the first segment and the second segment, where the intermediate segment is devoid of adhesive, where the intermediate segment is smaller than the first segment and smaller than the second segment.

2. A method for non-invasive repositioning of sagging skin, cellulite and fat tissue as set forth in claim 1 wherein said first segment and said second segment are attached to a thigh of an individual.

3. A method for non-invasive repositioning of sagging skin cellulite and fat tissue as set forth in claim 1 wherein said first segment and said second segment are attached to an arm of an individual.

4. A method for non-invasive repositioning of sagging skin, cellulite and fat tissue as set forth in claim 1 wherein said first segment and said second segment are attached to a stomach of an individual.

5. A method for non-invasive repositioning of sagging skin, cellulite and fat tissue as set forth in claim 1 wherein said first segment and said second segment are attached to buttocks of an individual.

6. A method for non-invasive repositioning of sagging skin, cellulite and fat tissue as set forth in claim 1 including the additional steps of removing said first and second segments from said skin and thereafter reapplying.

7. The method of claim 1, wherein an entirety of the continuous flexible tape is at least one of translucent or transparent.

* * * * *